United States Patent
Osypka

(10) Patent No.: US 7,949,402 B2
(45) Date of Patent: May 24, 2011

(54) NEURO-STIMULATION AND ABLATION SYSTEM

(75) Inventor: Thomas P. Osypka, Palm Harbor, FL (US)

(73) Assignee: Neuropoint Medical, Inc., Palm Harbor, FL (US)

( * ) Notice: Subject to any disclaimer, the term of this patent is extended or adjusted under 35 U.S.C. 154(b) by 421 days.

(21) Appl. No.: 11/643,462

(22) Filed: Dec. 21, 2006

(65) Prior Publication Data

US 2007/0219547 A1    Sep. 20, 2007

Related U.S. Application Data

(60) Provisional application No. 60/754,051, filed on Dec. 27, 2005.

(51) Int. Cl.
*A61N 1/00* (2006.01)
(52) U.S. Cl. .......................................................... 607/46
(58) Field of Classification Search .............. 607/2, 43, 607/46, 52, 57, 59, 115, 116, 117, 118; 128/897–899; 606/27, 31, 41, 42
See application file for complete search history.

(56) References Cited

U.S. PATENT DOCUMENTS

| | | |
|---|---|---|
| 4,374,527 A | 2/1983 | Iversen |
| 4,538,624 A | 9/1985 | Tarjan |
| 4,549,556 A | 10/1985 | Tarjan et al. |
| 5,121,754 A | 6/1992 | Mullett |
| 5,344,439 A | 9/1994 | Otten |
| 5,370,109 A | 12/1994 | Cuny |
| 5,433,198 A * | 7/1995 | Desai ............................ 600/374 |
| 5,450,842 A | 9/1995 | Tovey et al. |
| 5,733,322 A | 3/1998 | Starkebaum |
| 5,782,828 A * | 7/1998 | Chen et al. ...................... 606/42 |
| 6,066,165 A | 5/2000 | Racz |
| 6,258,086 B1 | 7/2001 | Ashley et al. |
| 6,447,443 B1 * | 9/2002 | Keogh et al. .................... 600/37 |
| 6,671,544 B2 | 12/2003 | Baudino |
| 6,728,579 B1 * | 4/2004 | Lindgren et al. ............... 607/116 |
| 2002/0138091 A1 | 9/2002 | Pflueger |
| 2003/0092303 A1 | 5/2003 | Osypka |
| 2004/0019381 A1 | 1/2004 | Plueger |
| 2005/0060006 A1 | 3/2005 | Pflueger et al. |
| 2005/0261754 A1 * | 11/2005 | Woloszko ....................... 607/99 |
| 2005/0283148 A1 | 12/2005 | Janssen et al. |
| 2006/0041295 A1 | 2/2006 | Osypka |

\* cited by examiner

*Primary Examiner* — Eric D Bertram
*Assistant Examiner* — Elizabeth K So
(74) *Attorney, Agent, or Firm* — Scott D. Wofsy; Edwards Angell Palmer & Dodge LLP

(57) ABSTRACT

The invention provides a system for treating chronic pain including a lead configured and adapted to be percutaneously implanted into an epidural space of a spinal cord, a stimulation generator that delivers electrical stimulation to the spinal cord through the lead to precisely locate the treatment area, and an ablation generator that delivers ablation energy to the treatment area through the same lead to inhibit the chronic pain. The invention also provides a method for treating chronic pain, including providing a lead, inserting the lead percutaneously into the epidural space, locating the treatment area by probing the epidural space while the lead sends electrical stimulation signals, and then ablating the treatment area.

5 Claims, 4 Drawing Sheets

NEURO-STIMULATION AND ABLATION SYSTEM

CROSS-REFERENCE TO RELATED APPLICATION

This application claims benefit of priority to U.S. Provisional Application Ser. No. 60/754,051 filed Dec. 27, 2005, incorporated herein by reference in its entirety.

BACKGROUND OF THE INVENTION

1. Field of the Invention

The present invention relates to a system and method for treating chronic pain through minimally invasive surgery. Particularly, the present invention is directed to a method and system for precisely locating a treatment location on the spinal cord using neuro-stimulation and then ablating the nerves of the spinal cord adjacent to the treatment area.

2. Description of Related Art

It is commonly known that pain persisting for more than three months, known as chronic pain, can be effectively treated with spinal cord stimulation (SCS). Spinal cord stimulation is currently performed with an implantable stimulation system consisting of an implantable pulse generator or two implantable lead systems having up to eight electrodes placed along the lead body. The lead system is electrically connected to the generator. The output of the generator is current controlled. A typical lead system has eight or sixteen channels that can deliver energy to as many as sixteen electrodes. The typical system also has one pulse generator and two lead systems connected in a dual head system to the pulse generator, each lead having eight electrically independent electrodes. Such systems are currently available from Medtronic, Inc., Advanced Neuromodulation Systems, Inc., and Advanced Bionics Corporation. Even though these implantable systems can treat chronic pain with a limited success rate, these systems have to be permanently implanted, have to be exchanged once the battery is depleted, or have to be recharged through an external battery charging system.

It is also well known in the art that ablating the affected area of the spinal cord can alleviate chronic pain on a long-term basis or even on a permanent basis. U.S. patent application Pub. No. 2005/0283148 to Janssen et al., and U.S. patent application Pub. No. 2005/0060006 to Pflueger et al. describe methods and devices for ablating nerve tissue. One means of ablating nerve tissue is through the use of RF energy delivered by electrodes implanted near the target tissue. Electrodes implanted within the spinal canal, for example, can be used to ablate tissues along the spinal cord to provide long term or even permanent relief to patients suffering chronic pain.

Such conventional methods and systems generally have been considered satisfactory for their intended purpose. However, pinpointing the exact location in the epidural space for ablation can be difficult when ablation electrodes are directed anatomically into the treatment location. Solutions to this problem have been developed to allow for directing ablation electrodes into place visually. Such visual techniques include guiding radio opaque ablation catheters fluoroscopically, or using optic fibers with cameras to visually guide the ablation electrodes into place.

However, even visual location techniques can fail to be successful or reliable. Physicians cannot always visually identify the precise location of the tissue which if ablated will alleviate the chronic pain. Guesswork is often involved and physicians may need to ablate large amounts of tissue in order to insure complete treatment of a small amount of target tissue. As a result, the target nerves are often ablated along with numerous otherwise healthy nerves. Unnecessary ablation of healthy nerves is detrimental because ablation can be permanent. There still remains a continued need in the art for a system and method that can reliably pinpoint the specific spinal nerve tissue for precise ablation. There also remains a need in the art for such a system and method that are inexpensive and easy to make and use. The present invention provides a solution for these problems.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied herein and broadly described, the invention includes a system for treating chronic pain having a lead configured and adapted to be percutaneously implanted into an epidural space defined by a spinal canal. The system also includes a stimulation generator that may selectively be connected to the lead electrically. The stimulation generator is operative to deliver electrical stimulation to the spinal cord through an electrode in order to determine a treatment location. The lead preferably includes a plurality of electrodes. The system also includes an ablation generator that may selectively be connected to the lead electrically. The ablation generator is operative to deliver ablation energy to the treatment location to ablate spinal cord tissue.

In accordance with a further aspect of the invention, the system can further include a switch operative to allow a user to switch the system from a stimulation mode in which only the stimulation generator is electrically connected to the lead, to an ablation mode in which only the ablation generator is electrically connected to the lead.

In accordance with another aspect of the invention, the ablation generator can deliver ablation energy in a temperature-controlled manner. The system can further include a temperature sensor operably coupled to the ablation generator. The temperature sensor is preferably operative to facilitate temperature-controlled delivery of ablation energy to the treatment location by providing feedback to the ablation generator. The temperature sensor can be located within the lead. Moreover, the temperature sensor can be a thermocouple located within the electrode. Preferably the lead includes a plurality of electrodes, each electrode having a thermocouple operably connected thereto.

In accordance with still another aspect of the invention, a processor can be provided. The processor is operably coupled to the stimulation and ablation generators, and is adapted and configured to control the output levels of stimulation and ablation energy delivered to the spinal cord of the patient. The system can further include a machine-readable program containing instructions for controlling the processor to control the stimulation and ablation generators. The program includes means for instructing the processor to control the output levels of stimulation and ablation energy delivered to the spinal cord of the patient.

In accordance with yet another aspect of the invention, the lead can include an elongated body having opposed proximal and distal end portions, wherein the distal end portion is adapted for movement between a first state in which the distal end portion has a generally linear configuration and a second state in which the distal end portion has an undulating configuration. The lead can also include at least one electrode operatively associated with the distal end portion of the lead body. A connector means can be operatively associated with the proximal end portion of the lead body for connecting to the stimulation and ablation generators. A conductor means can extend through the lead body for conducting signals between the at least one electrode and the connector means. The generally linear configuration of the distal end portion in the first state can facilitate movement of the lead within the epidural space. The undulating configuration of the distal end portion in the second state can allow for the distal end portion of the lead body to exert an outward force on structures of the spinal canal once situated within the epidural space to affix the lead within the spinal canal.

The invention also includes a spinal cord stimulation system for treating chronic pain that includes a lead configured for implantation adjacent a treatment location of a spinal cord. The system also includes a stimulator for sending current controlled impulses to the treatment location by way of the lead. An ablation generator is included for sending temperature-controlled energy to the treatment location by way of the lead. A processor is configured to control the output levels of the stimulator and ablation generator. A switch is also provided that allows a user to alternate between sending stimulation and ablation energy to the treatment location. The ablation generator can have a temperature sensor embedded proximate the distal end of the lead for measuring the temperature during ablation. The lead preferably includes a plurality of electrodes and each electrode can include an embedded temperature sensor.

The invention also includes a method for treating chronic pain. The method includes providing an implantable lead having an electrode configured to deliver electrical stimulation and ablation energy to a treatment location along a patient's spinal cord. The method also includes inserting a lead percutaneously into the epidural space of the spinal cord of the patient. Next, the treatment location on the spinal cord is located by sending electrical stimulation through the lead to the electrode and probing with the lead in the epidural space until the electrode reaches the treatment location on the patient's spinal cord, where the electrical stimulation causes the patient to experience a physiological reaction indicative of the electrode contacting the treatment location. Then ablation energy is delivered to the electrode to ablate the nerve tissue proximate the treatment location.

In further accordance with the invention, the step of delivering ablation energy can further include controlling the ablation temperature by receiving feedback from a temperature sensor. Locating the treatment location can further include cycling stimulation signals through a plurality of electrodes provided in the lead. The method can further include the step of switching the lead from a stimulation mode, in which electrical stimulation is sent from a stimulation generator to the electrode, to an ablation mode in which ablation energy is sent from an ablation generator to the electrode. It is also envisioned that the method can further include controlling the output levels from the stimulation and ablation generators using a processor.

It is to be understood that both the foregoing general description and the following detailed description are exemplary and are intended to provide further explanation of the invention as claimed. The accompanying drawings, which are incorporated in and constitute part of this specification, are included to illustrate and provide a further understanding of the method and system of the invention. Together with the description, the drawings serve to explain the principles of the invention.

BRIEF DESCRIPTION OF THE DRAWINGS

So that those having ordinary skill in the art to which the present application appertains will more readily understand how to make and use the same, reference may be had to the drawings wherein.

These and other features of the system for treating chronic pain of the subject invention will become more readily apparent to those having ordinary skill in the art from the following description of exemplary embodiments.

DETAILED DESCRIPTION OF THE PREFERRED EMBODIMENT

Reference will now be made in detail to the present preferred embodiments of the invention, an example of which is illustrated in the accompanying drawings. The method and corresponding steps of the invention will be described in conjunction with the detailed description of the system.

The devices and methods presented herein may be used for treating chronic pain. The present invention is particularly suited for targeting the exact location of nerve tissue in the epidural space needing treatment, such as along the spinal cord, and ablating the tissue at that location.

In accordance with the invention, a system for treating chronic pain is provided including a lead configured and adapted to be percutaneously implanted into the epidural space within the spinal canal. A stimulation generator is selectively connected to the lead electrically. The stimulation generator is operative to deliver electrical stimulation to the spinal cord through an electrode in order to determine the treatment location. An ablation generator, also selectively connected to the lead electrically, is operative to deliver ablation energy to the treatment location to ablate spinal cord tissue.

Figure 1:
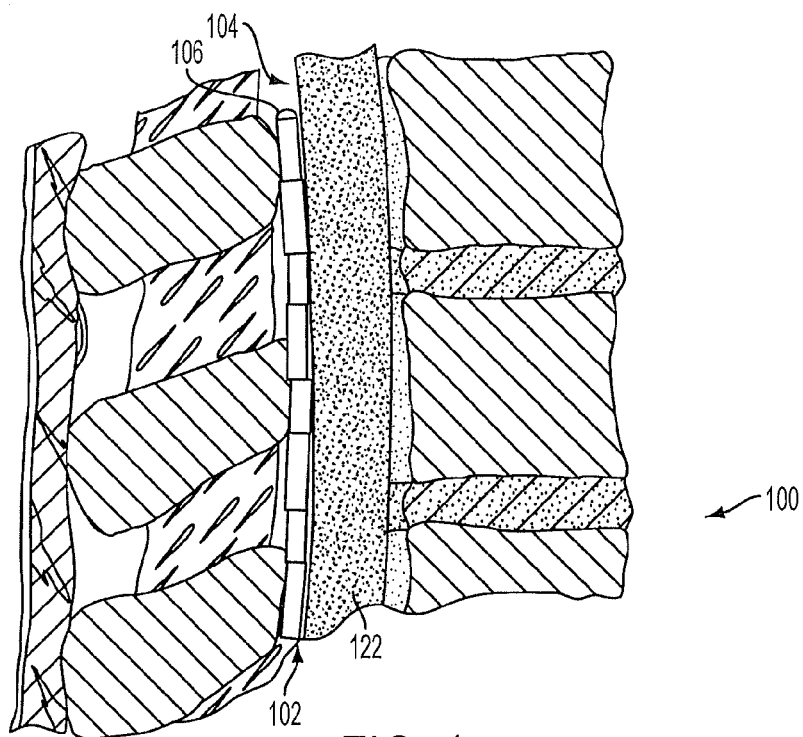
FIG. 1 is a side view of a neurological epidural lead according to a first representative embodiment of a system for treating chronic pain wherein the lead is being implanted in the epidural space of the spinal canal.

For purposes of explanation and illustration, and not limitation, a partial view of an exemplary embodiment of the system in accordance with the invention is shown in FIG. 1 and is designated generally by reference number 100. Other embodiments of a system in accordance with the invention, or aspects thereof, are provided in FIGS. 2-5, as will be described.

Figure 2:
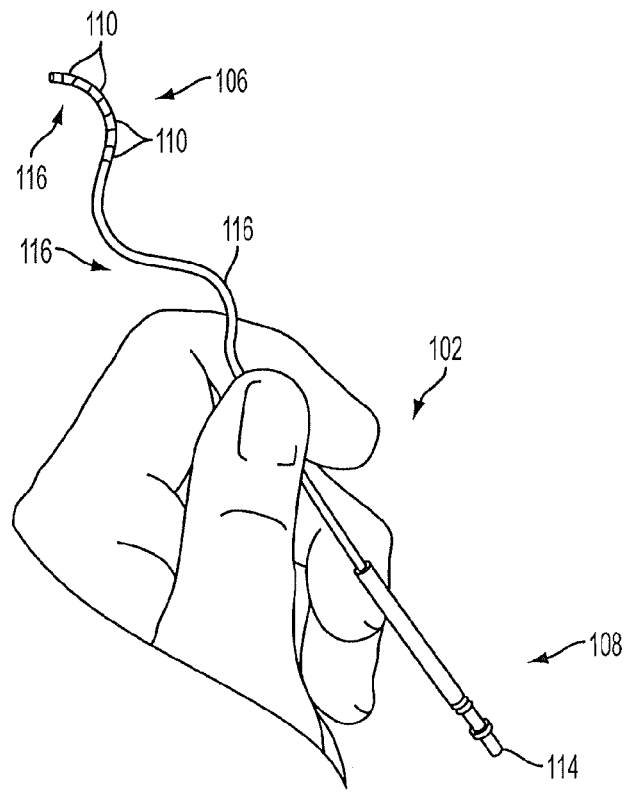
FIG. 2 is a side view of the lead of FIG. 1, showing the lead in an undulating configuration and held by a user prior to percutaneous implantation.

In accordance with the invention, a lead is provided that is configured and adapted for percutaneous implantation into an epidural space defined by the spinal canal of the patient. For purposes of illustration and not limitation, as embodied herein and as depicted in FIGS. 1 and 2, system 100 is provided with a lead 102. Lead 102 has a distal end 106 and proximal end 108 and is configured and adapted for percutaneous implantation into a cylindrical or crescent shaped epidural space 104 defined by a patient's spinal canal. Lead 102 can access epidural space 104 through a sacral hiatus, through an opening made in the ligamentum flavum, or through any other suitable means of access. The typical dimensions of lead 102 can vary according to application, but it is preferable that the diameter be between about 0.04 inches (1 mm) and about 0.08 inches (2 mm), with the length between about 2 feet (60 cm) and about 6.6 feet (200 cm).

It is possible to practice the invention with traditional neurological epidural leads. Materials for the main body of lead 102 include implantable grade silicone or polyurethane, however, the invention can be practiced with any other suitable material. Traditional neurological epidural leads are generally straight or linear because straight leads can more easily navigate the contours of epidural space 104. However, straight leads also move easily after being set in place. Thus straight leads that have been properly implanted are often inadvertently moved away from the desired location when the lead is disturbed. This necessitates relocating the lead back to the proper location.

Figure 3:
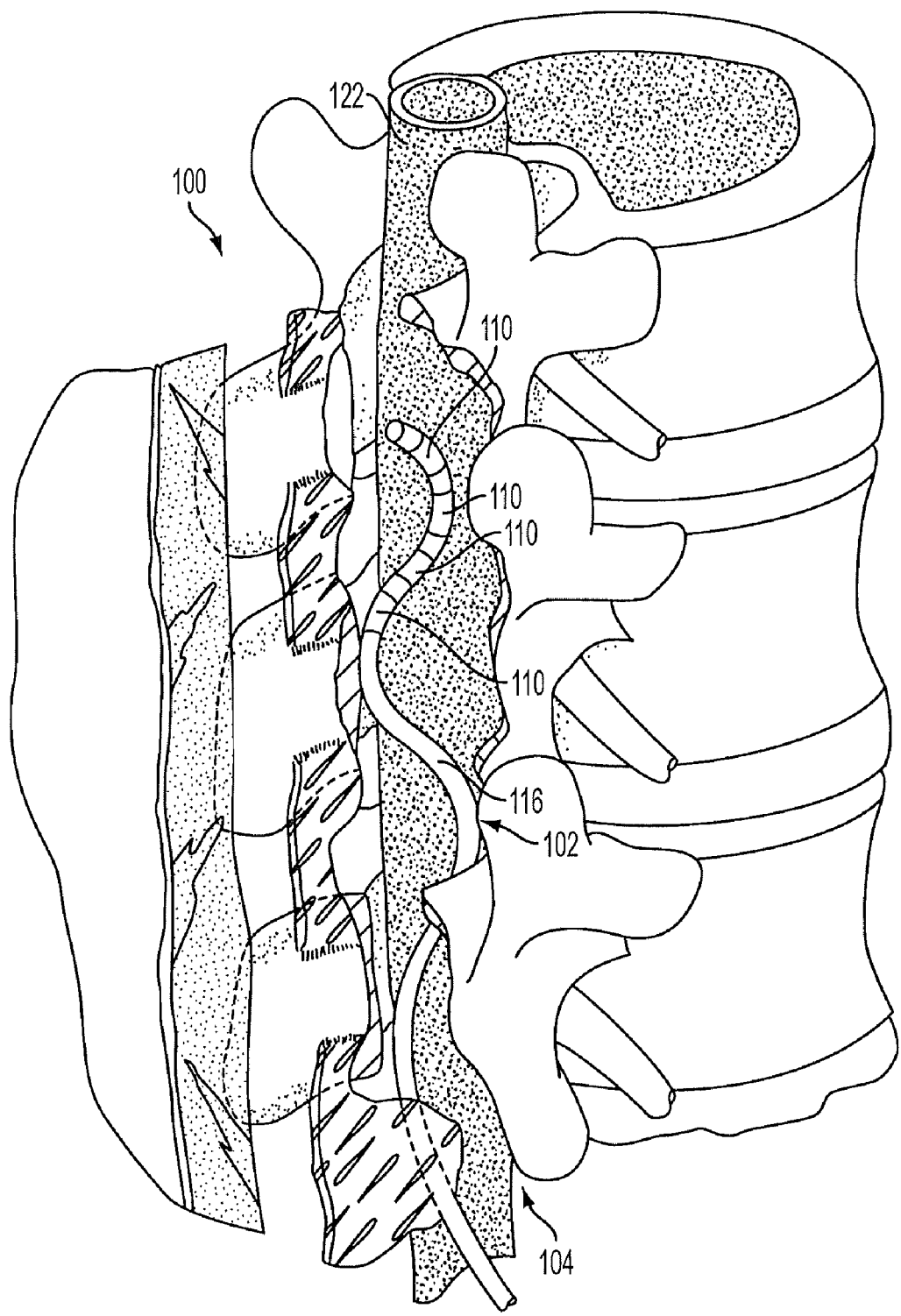
FIG. 3 is a perspective view the lead of FIG. 1, showing the lead implanted in the epidural space of the spinal canal and having an undulating configuration that causes the lead to be affixed within the epidural space.

It is therefore preferable for lead 102 to have a material predisposition to be undulated, rather than straight. FIG. 2 shows an undulated lead 102 prior to implantation. During implantation, a guide wire (not shown) is inserted into a central lumen within the length of lead 102. The guide wire straightens lead 102 for easy navigation within epidural space 104. Once lead 102 is in the proper location, the guide wire can be withdrawn and lead 102 relaxes back into its undulated configuration, in which undulations 116 lodge lead 102 securely within epidural space 104 (as shown in FIG. 3). Leads capable of this manner of positive fixation, and procedures for implantation of the same, are more fully described in U.S. patent application Pub. No. 2006/0041295, which is incorporated by reference herein in its entirety.

A plurality of electrodes 110 is disposed about lead 102 at distal end 106. It is possible to practice embodiments of the invention with only one electrode 110, but it is preferable to have more than one. Electrodes 110 can be made of a variety of materials, including platinum iridium (PT/Ir), stainless steel, or any other suitable material known in the art. Electrodes 110 are electrically connected to conductors 112 within lead 102 (shown schematically in FIG. 5). Conductors 112 terminate at connector 114 at proximal end 108 of lead 102. Electrodes 110 are each independently connected to connector 114 and can thus be independently connected to electrical components, such as those described below. Connector 114 is configured for connecting with switch 120, shown in FIG. 4, either directly or via an extension cable.

Figure 4:
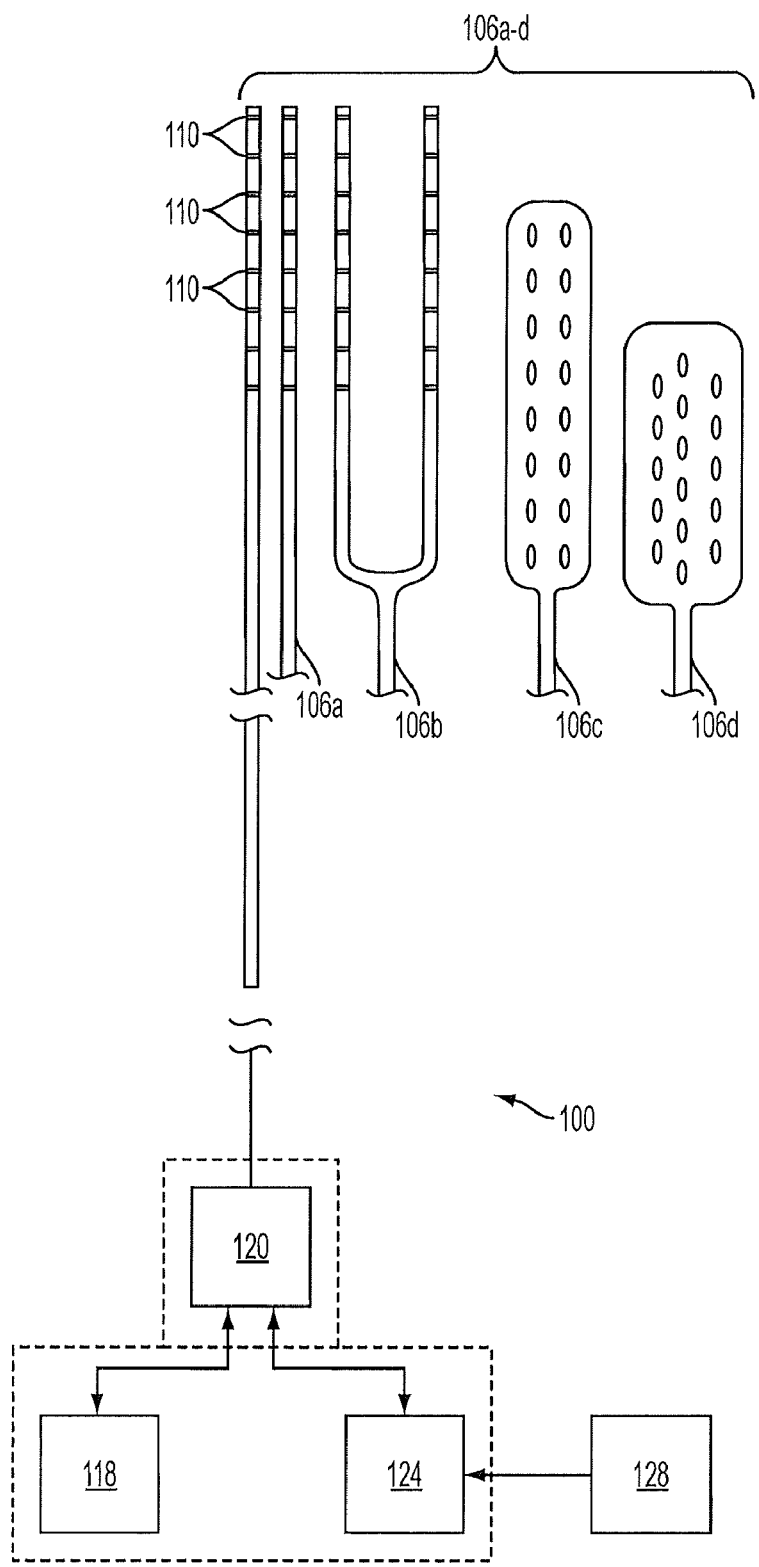
FIG. 4 is a diagram of a system for treating chronic pain in accordance with the present invention, showing the relationships between the lead, the stimulation generator, the ablation generator, and the processor. Several different examples of leads are shown.
Figure 5:
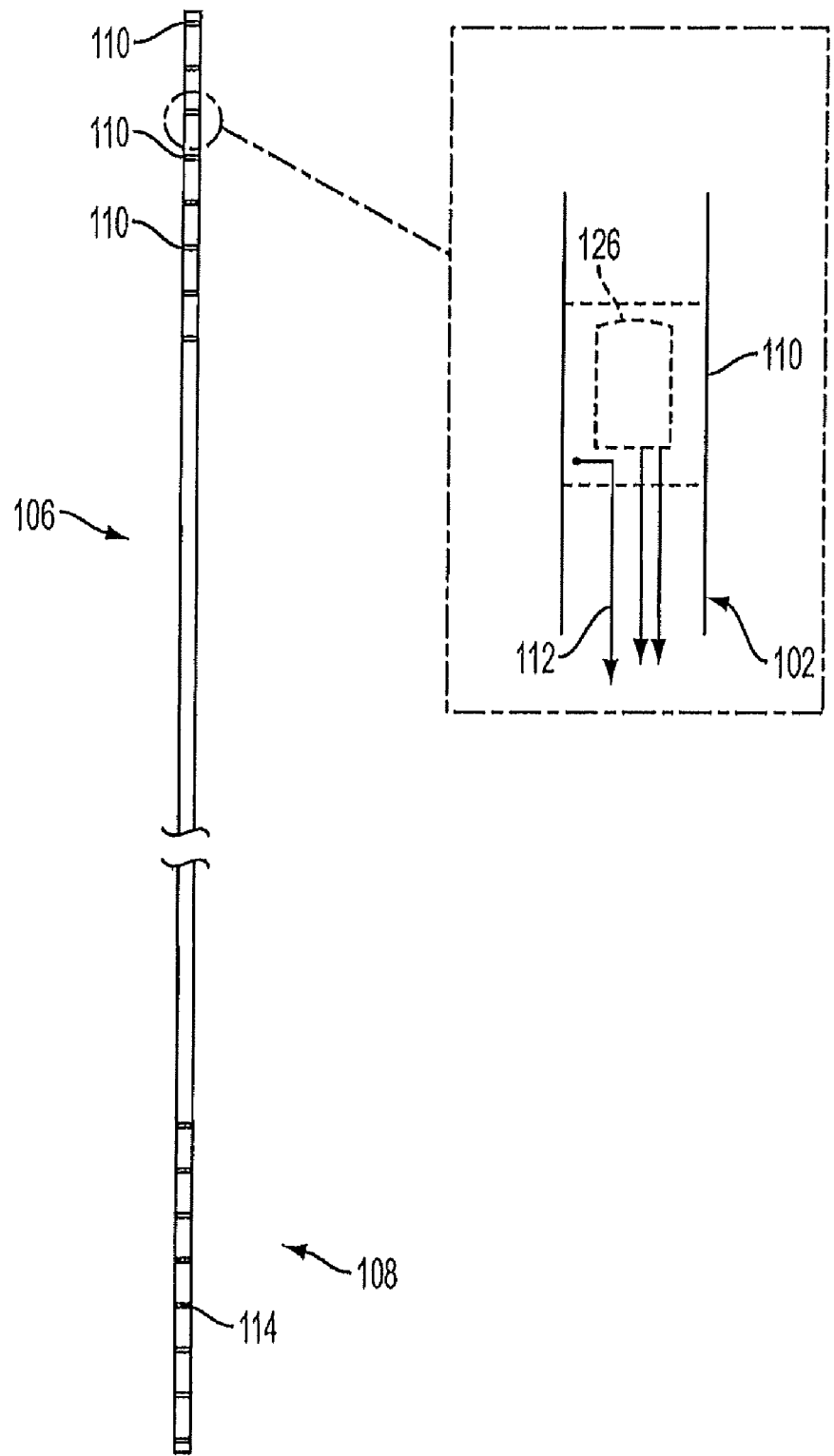
FIG. 5 is a magnified side view of the lead of FIG. 1, showing a temperature sensor embedded within one of the electrodes, as well as the conductors running from the electrode and temperature sensor, along the length of the lead toward the ablation and stimulation generators.

A variety of different distal lead sections are possible, as shown by way of example and not limitation in FIG. 4. Examples of the many possible configurations of distal end 106 of lead 102 include round (106a), forked (106b), and paddle shaped (106c and 106d). These configurations and others readily appreciated by those of ordinary skill in the art can be used alone or in combination without departing from the spirit and scope of the invention.

In further accordance with the invention, a stimulation generator is provided that operates to deliver electrical stimulation to the spinal cord through an electrode in order to determine a treatment location. The stimulation generator is selectively connected to the lead electrically.

For purposes of illustration and not limitation, as embodied herein and as depicted in FIG. 4, system 100 includes stimulator 118. When a user throws switch 120 to select stimulator 118, stimulator 118 connects electrically to electrodes 110 of lead 102. The function of stimulator 118 is to send current controlled electrical impulses out to electrodes 110 of implanted lead 102 as stimulation signals for nerve tissue. The stimulation signals serve an important function in precisely locating the nerve tissue needing ablation.

It is well established in the art that proper electrical stimulation can inhibit nerve functions and thereby alleviate pain on a temporary basis, including chronic pain. Thus if electrodes 110 are adjacent to nerve tissue that conducts chronic pain signals, stimulator 118 can send the stimulation signals needed to inhibit the pain signals and provide relief. When searching for spinal nerve tissue to be ablated, a physician can probe epidural space 104 with lead 102 while actively sending stimulation signals. When the active lead 102 contacts the treatment location, there will be a physiological reaction in the patient that indicates to the physician that an electrode 110 is in contact with the treatment location. Typically the physiological reaction is a tingling or buzzing sensation, or cessation of the chronic pain, but it can also be a muscular contraction, or other reactions known in the art. Once the indicative physiological reaction occurs, electrodes 110 of lead 102 are in the precise location to treat the chronic pain through ablation, as described in detail below.

Stimulator 118 can send single phase (negative only) or biphasic pulses (negative or positive) to electrodes 110. Typical output specifications for stimulator 118 include a pulse frequency between about 40 Hz and about 1200 Hz, a pulse duration between about 10 μs to about 2000 μs, a pulse amplitude between about 1 mA to about 20 Ma, and a voltage of between about 1 V to about 12 V. However, those of ordinary skill in the art will readily appreciate that these specifications can be varied without departing from the spirit and scope of the invention. Preferably, stimulator 118 controls the voltage to provide a steady, preset current by measuring the impedance of system 100 as feedback. Typical specifications for stimulator 118 therefore include a measured impedance of about 100 Ohms (characteristic of low impedance) to about 4000 Ohms (indicative of high impedance or lack of good contact with spinal cord 122). Stimulator 118 can also have a number of independent channels. Any number of channels can be used, but preferably the number of channels is between about eight and about sixteen.

In further accordance with the invention, the system includes an ablation generator. For purposes of illustration and not limitation, as depicted in FIG. 4, system 100 includes ablation generator 124. Like stimulator 118, ablation generator 124 connects electrically to lead 102 through switch 120 when a user throws switch 120 to select ablation generator 124. Switch 120 thus switches system 100 between a stimulation mode in which stimulator 118 is actively connected to lead 102, and an ablation mode in which ablation generator 124 is actively connected to lead 102. Ablation generator 124 serves to send ablation energy to electrodes 110 with RF pulses, as is well known in the art, to ablate the targeted tissue in a precise manner with little or no effect on the remaining nervous system tissues.

Ablation generator 124 is able to control the temperature of ablation by adjusting the RF energy output in view of temperature feedback. The controller can use closed loop controls such as fuzzy logic, proportional-integral-derivatives (PID), or any other suitable method or combination of methods. For this purpose, a temperature sensor 126 is provided within each electrode 110. Temperature sensors 126 are electrically coupled to ablation generator 124 in order to provide temperature measurements as feedback to control the temperature of ablation. A variety of types of temperature sensors 126 can be used, including thermocouples, thermistors, or any other suitable sensor. Further, while temperature sensors 126 are shown embedded inside electrodes 110 in FIG. 5, it is possible to locate them in other suitable locations as long as they can provide the needed temperature measurements.

A user can select the target temperature, length of time for ablation, and other parameters (including safety and security parameters) for ablation generator 124 on a case by case basis. Typical specifications for ablation generator 124 include an ablation frequency of about 200 kHz to about 1000 kHz, a target temperature between about 104° F. (40° C.) and about 140° F. (60° C.), an energy source of between about 10 W and about 75 W, and a set duration of ablation between about 5 seconds and about 90 seconds. However, those of ordinary skill in the art will readily appreciate that these parameters can be varied without departing from the spirit and scope of the invention.

In further accordance with the invention, a system for treating chronic pain includes a processor operably coupled to the stimulator and ablation generator. The processor is adapted and configured to control the output levels of stimulation and ablation energy delivered to the spinal cord of a patient.

For purposes of illustration and not limitation, as depicted in FIG. 4, system 100 includes processor 128. Processor 128 operates to set the electrical output settings of stimulator 118 and ablation generator 124. Processor 128 can control the channels of stimulator 118 individually. Further, processor 128 can control temperature, duration, and channel parameters for ablation. Processor 128 can further include a machine-readable program with instructions for controlling stimulator 118 and ablation generator 124. The program instructs processor 128 to control the output levels of stimulation and ablation energy delivered to spinal cord 122 of a patient. These levels can be preset values, or processor 128 can take the values as input from a physician or other user of system 100.

In accordance with another aspect of the invention, a method for treating chronic pain is provided. The method includes providing an implantable lead having an electrode configured to deliver electrical stimulation and ablation energy to a treatment location of the spinal cord of a patient. The lead is inserted percutaneously into an epidural space of the patient's spinal cord. The user then determines the treatment location by sending electrical stimulation signals through the lead to the electrode and probing with the lead in the epidural space until the electrode reaches a treatment location on the patient's spinal cord. The user will know the electrode has reached the treatment location when the electrical stimulation causes the patient to experience a physiological reaction indicative of the electrode reaching the treatment location. Ablation energy is then delivered to the electrode to ablate the nerve tissue proximate the treatment location.

For purposes of illustration and not limitation, as embodied herein and as depicted in FIGS. 1-5, the method for treating chronic pain includes providing a lead, such as lead 102 described above. The lead is inserted percutaneously into an epidural space of the spinal cord of the patient, as shown in FIGS. 1 and 3. The user can place the lead in the general area needing treatment by directing the lead anatomically, fluoroscopically, optically, or by any other suitable means.

The precise treatment location is then determined by sending electrical stimulation signals through the lead to the electrodes thereon, such as described above by using a system such as system 100 described herein. With the electrical stimulation signals active, the user of the lead manipulates the lead to probe around the epidural space, searching for the treatment location. The user will know the precise treatment location has been reached when the patient exhibits a physiological reaction to the electrical stimulation. Typically, the physiological reaction is as a tingling or buzzing sensation that may supplant the chronic pain. However, other physiological reactions can also indicate that the lead is in the proper place, such as a reduction or cessation of the chronic pain, muscular contractions, or other reactions known in the art. The probing can be further enhanced if the lead has multiple electrodes. The user can cycle through the electrodes, delivering stimulation signals to each in turn, to determine which electrode is most precisely adjacent the treatment area. Traditional leads that are generally straight or linear can be used, but preferably the lead is elastic and has a curved or undulated configuration in its distal end when in an unloaded state, as shown in FIG. 2.

When an electrode is in place at the treatment location, the user can then switch the lead from stimulation mode to ablation mode. The electrode then delivers ablation energy to ablate the nerve tissue in the treatment location. The ablation energy can be delivered in a temperature-controlled manner, as described above. It is even possible for the user to control the ablation to inhibit the chronic pain temporarily, or permanently, as is known in the art of nerve ablation. The greater the ablation in terms of temperature and duration, the longer the relief will last. A processor, as described above, can control both the ablation and stimulation.

The methods and systems of the present invention, as described above and shown in the drawings, provide for a system and method for treating chronic pain. The systems and methods disclosed herein have superior properties including the ability to precisely locate and treat the spinal nerve tissue from which chronic pain stems. It will be apparent to those skilled in the art that various modifications, variations, and combinations can be made in the device and method of the present invention without departing from the spirit or scope of the invention. Thus, it is intended that the present invention include modifications, variations, and combinations that are within the scope of the appended claims and their equivalents.

What is claimed is:

1. A method for treating chronic pain comprising:
    a. providing an implantable lead having an electrode configured to deliver electrical stimulation and ablation energy to a treatment location of a spinal cord of a patient;
    b. inserting the lead percutaneously into an epidural space of the spinal cord of the patient;
    c. locating the treatment location on the spinal cord by:
        i. sending electrical stimulation through the lead to the electrode; and
        ii. probing with the lead in the epidural space until the electrode reaches the treatment location on the patient's spinal cord where the patient experiences a physiological reaction from the electrical stimulation indicative of the electrode contacting the treatment location; and
    d. delivering ablation energy to the electrode to ablate nerve tissue proximate the treatment location.

2. The method recited in claim 1, wherein the step of delivering ablation energy includes controlling ablation temperature by receiving feedback from a temperature sensor.

3. The method recited in claim 1, wherein the lead has a plurality of electrodes, and wherein the locating step includes cycling through the plurality of electrodes with stimulation signals.

4. The method recited in claim 1, further comprising the step of switching the lead from a stimulation mode, in which electrical stimulation is sent from a stimulation generator to the electrode, to an ablation mode, in which ablation energy is sent from an ablation generator to the electrode.

5. The method recited in claim 4, further comprising the step of controlling the output levels for the stimulation and ablation generators using a processor.

\* \* \* \* \*